US011660402B2

(12) United States Patent
Okihara

(10) Patent No.: US 11,660,402 B2
(45) Date of Patent: May 30, 2023

(54) SYRINGE AND PREFILLED SYRINGE

(71) Applicant: TERUMO KABUSHIKI KAISHA, Tokyo (JP)

(72) Inventor: Hitoshi Okihara, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 448 days.

(21) Appl. No.: 16/862,874

(22) Filed: Apr. 30, 2020

(65) Prior Publication Data

US 2020/0268982 A1  Aug. 27, 2020

Related U.S. Application Data

(63) Continuation of application No. PCT/JP2018/040413, filed on Oct. 30, 2018.

(30) Foreign Application Priority Data

Oct. 31, 2017 (JP) .............................. JP2017-210440

(51) Int. Cl.
*A61M 5/32* (2006.01)
*A61M 5/31* (2006.01)
(52) U.S. Cl.
CPC ... *A61M 5/3202* (2013.01); *A61M 2005/3109* (2013.01); *A61M 2005/3125* (2013.01)
(58) Field of Classification Search
CPC ........ A61M 5/3202; A61M 2005/3104; A61M 2005/3106
See application file for complete search history.

(56) References Cited

U.S. PATENT DOCUMENTS

| 4,172,457 A | 10/1979 | Choksi et al. |
| 5,807,345 A * | 9/1998 | Grabenkort ......... A61M 5/3134 604/199 |
| 5,857,580 A * | 1/1999 | Iidaka .................... B65D 41/60 215/354 |
| 2013/0338575 A1 | 12/2013 | Glocker et al. |

(Continued)

FOREIGN PATENT DOCUMENTS

| CN | 102961803 A | 3/2013 |
| EP | 3 042 678 A1 | 7/2016 |
| EP | 3 520 847 A1 | 8/2019 |

(Continued)

OTHER PUBLICATIONS

The extended European Search Report dated Jul. 17, 2020, by the European Patent Office in corresponding European Patent Application No. 18874321.5-1122. (9 pages).

(Continued)

*Primary Examiner* — Laura A Bouchelle
(74) *Attorney, Agent, or Firm* — Buchanan Ingersoll & Rooney PC

(57) ABSTRACT

In a syringe, which is a prefilled syringe, when a cap body is attached to a cylindrical portion, a first sealing section is compressed radially inward by an inner peripheral surface constituting an opening of the cylindrical portion, thereby sealing a distal end section of a flow path in a liquid-tight manner, and a second sealing section is compressed radially inward by an inner peripheral surface of a proximal end section of the cylindrical portion, thereby sealing a proximal end section of the flow path in a liquid-tight manner.

20 Claims, 12 Drawing Sheets

(56) References Cited

U.S. PATENT DOCUMENTS

2016/0184529 A1\* 6/2016 Okihara ................. A61M 5/28
604/199

FOREIGN PATENT DOCUMENTS

| JP | H43750 U | 1/1992 |
| JP | H08215307 A | 8/1996 |
| JP | 2009508781 A | 3/2009 |
| WO | 2015033951 A1 | 3/2015 |

OTHER PUBLICATIONS

International Search Report (PCT/ISA/210) dated Feb. 5, 2019, by the Japanese Patent Office as the International Searching Authority for International Application No. PCT/JP2018/040413.

\* cited by examiner

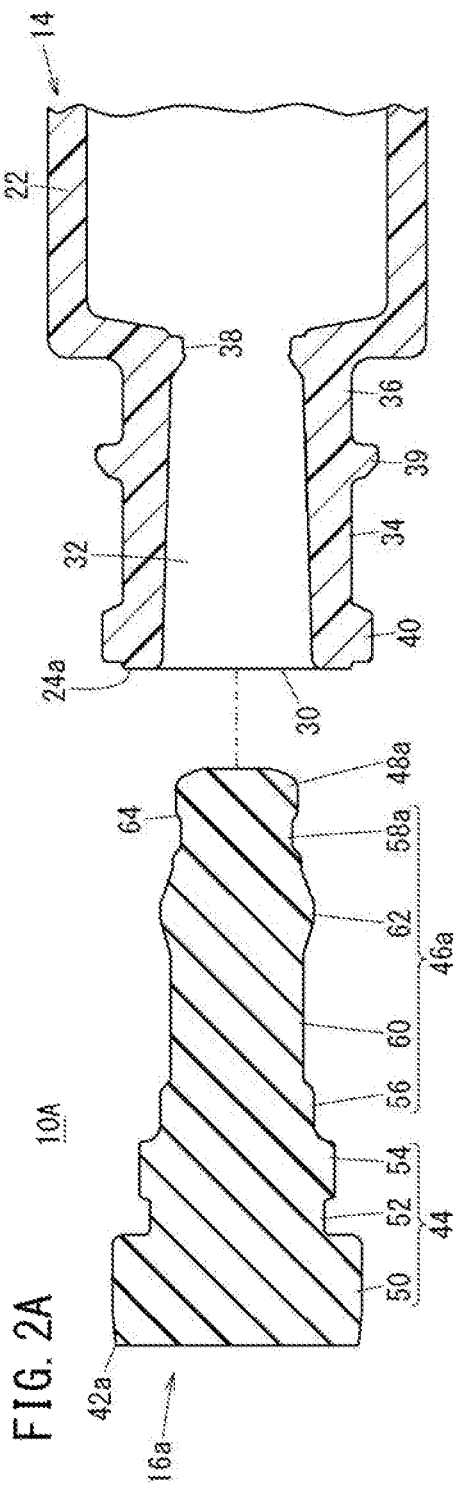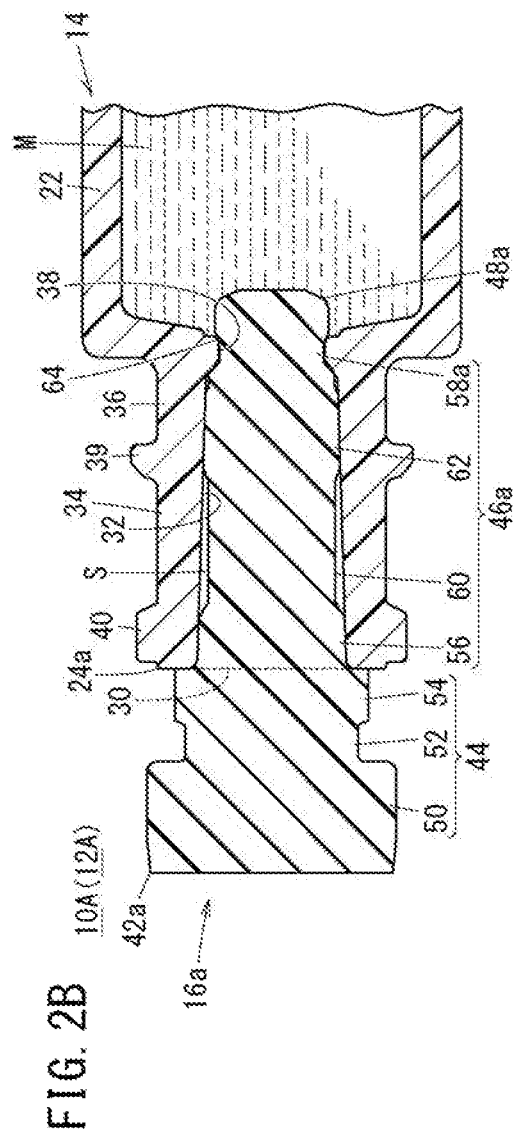

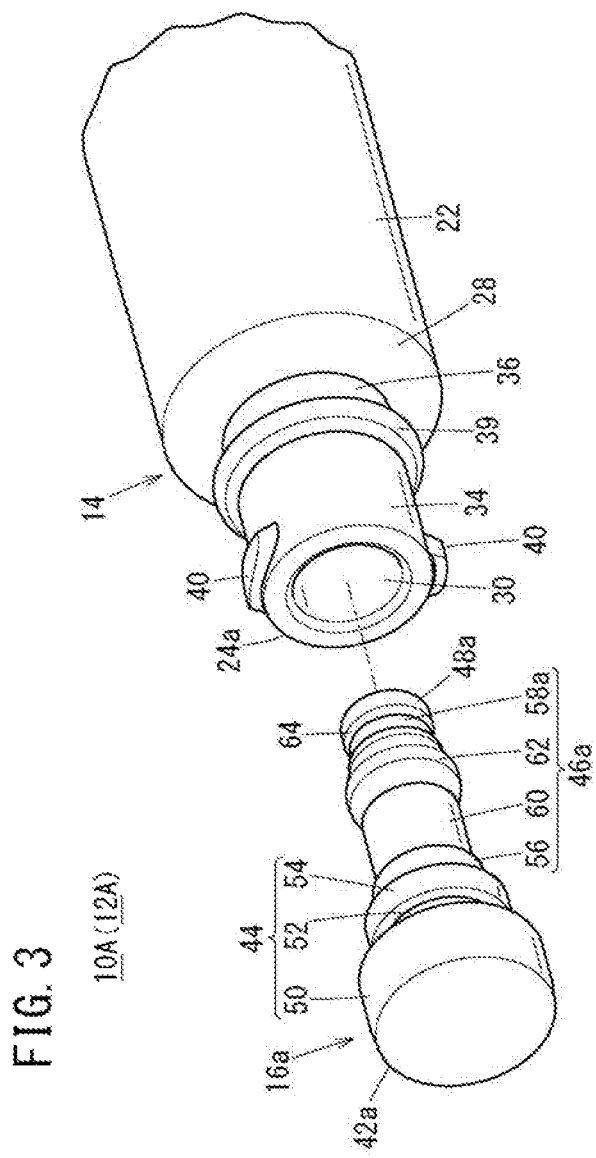

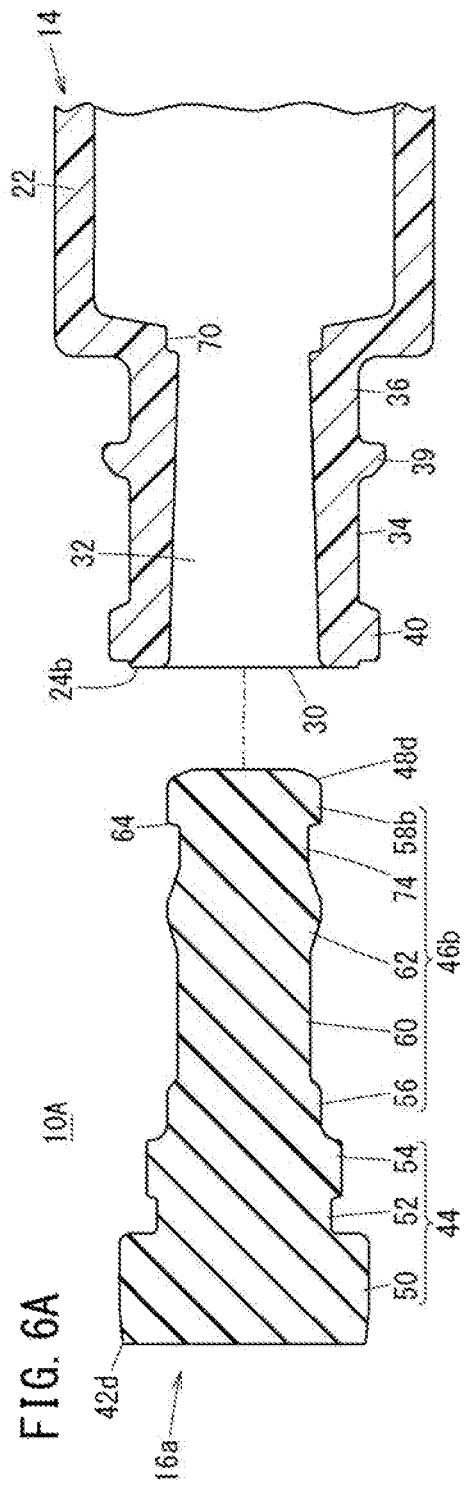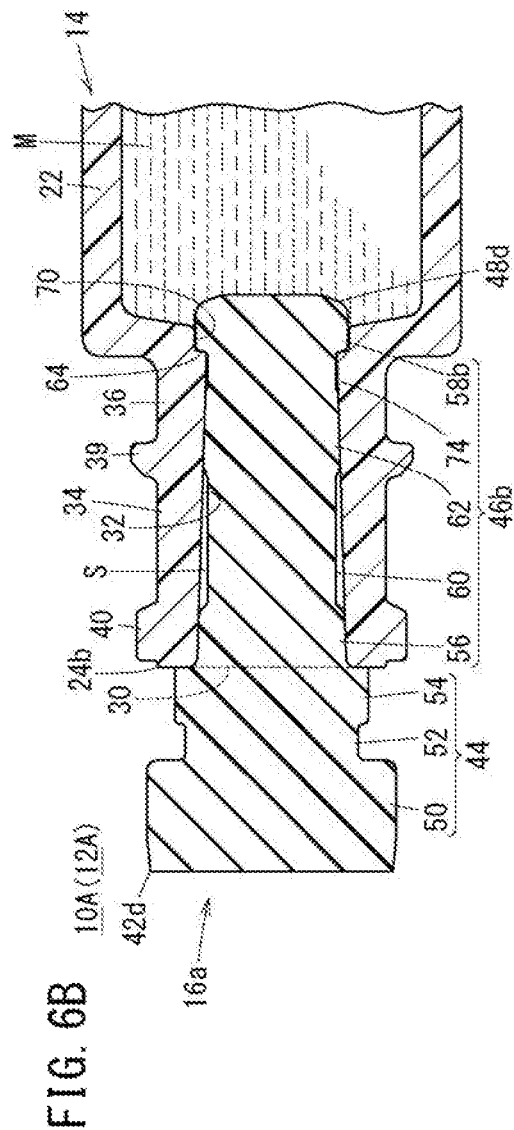

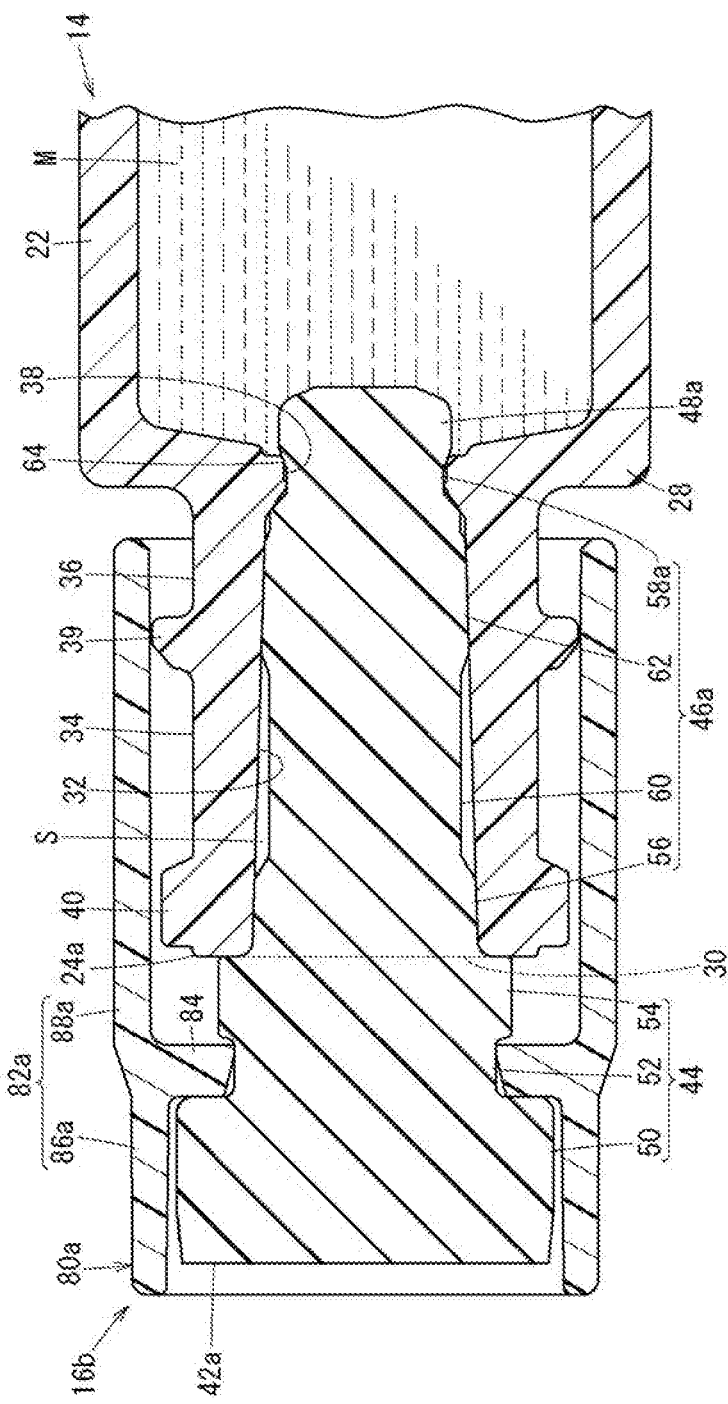

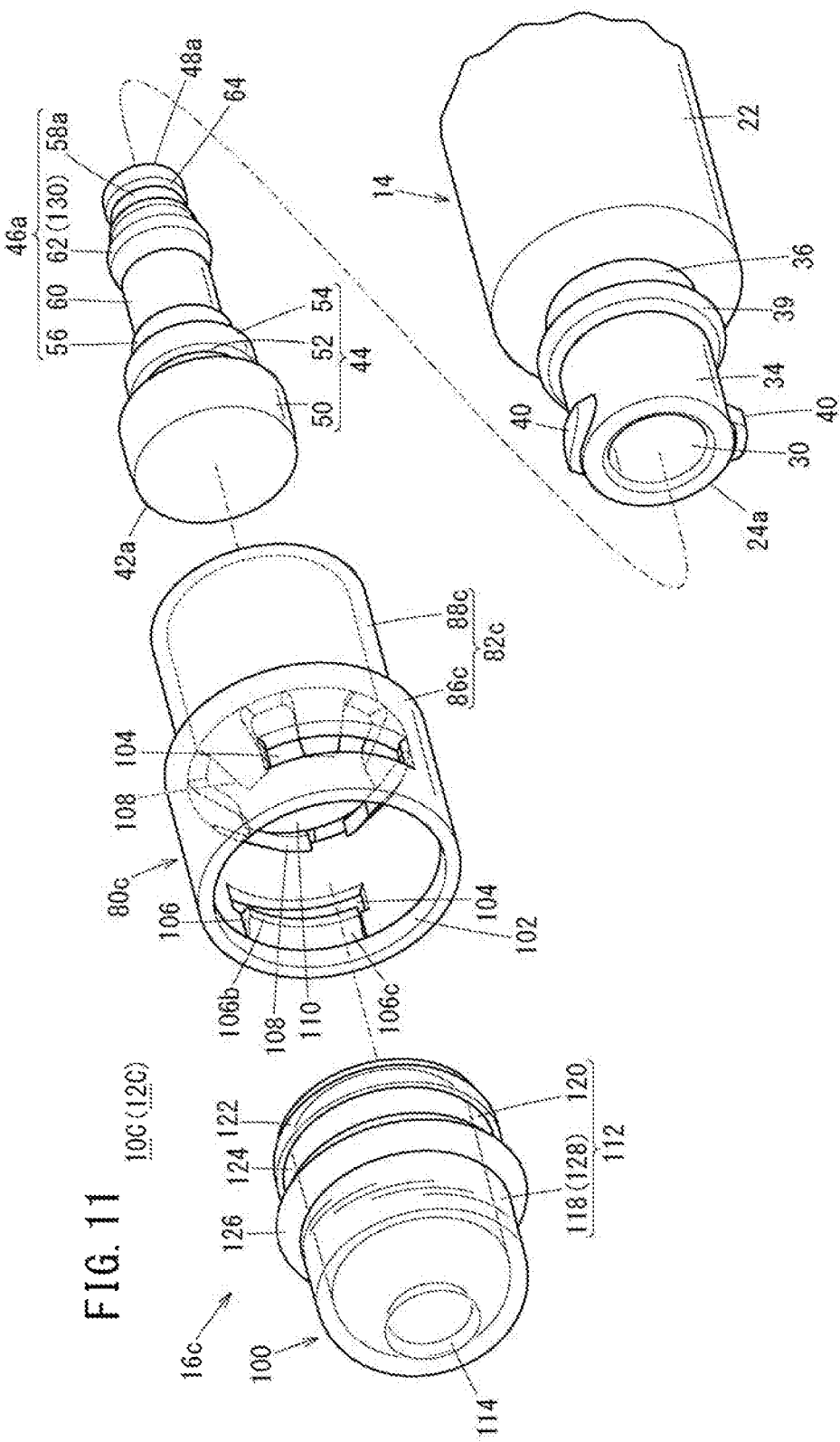

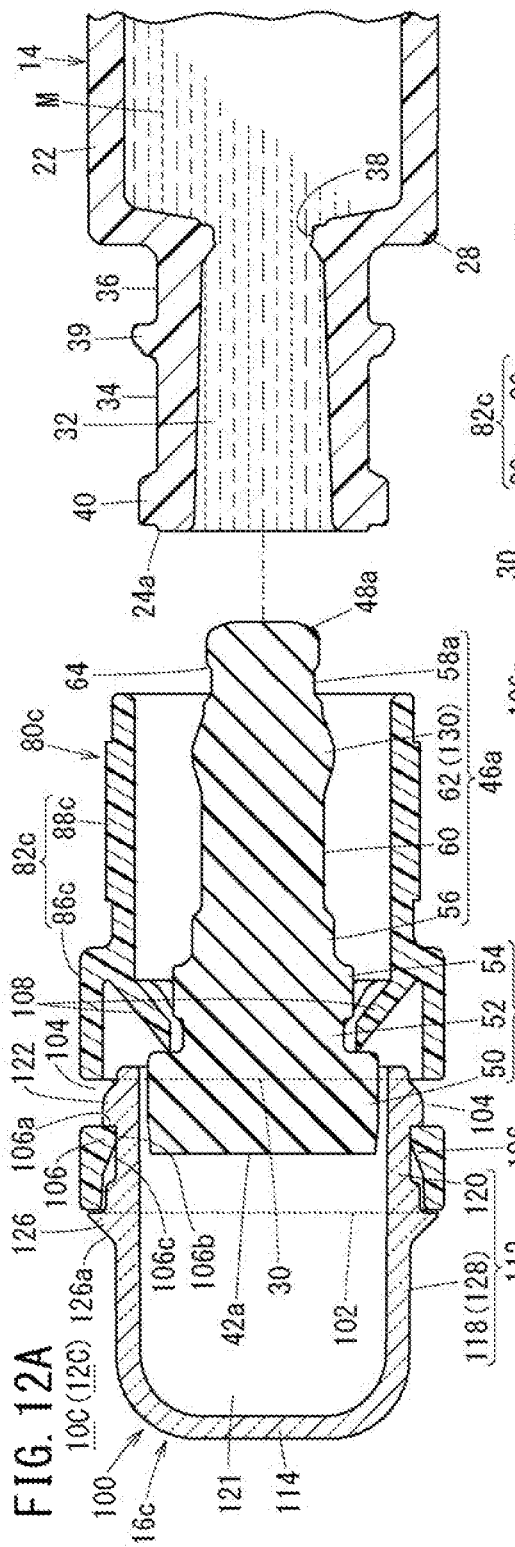

SYRINGE AND PREFILLED SYRINGE

CROSS-REFERENCES TO RELATED APPLICATIONS

This application is a continuation of International Application No. PCT/JP2018/040413 filed on Oct. 30, 2018, which claims priority to Japanese Application No. 2017-210440 filed on Oct. 31, 2017, the entire content of both of which is incorporated herein by reference.

FIELD OF THE DISCLOSURE

The present disclosure generally relates to a syringe and a prefilled syringe in which a cap body made of an elastic material is attached to a cylindrical portion of a barrel body.

BACKGROUND DISCUSSION

U.S. Pat. No. 4,172,457 discloses a syringe which includes a barrel body having a body portion which can be filled with a drug solution, and a cylindrical portion protruding from the body portion in a distal direction, and a cap inserted into the cylindrical portion. In this syringe, the outer peripheral surface of the cap is in contact with the inner peripheral surface of the cylindrical portion at a proximal end section of the cylindrical portion.

In the above-mentioned syringe, when the internal pressure of the body portion of the barrel body becomes higher than the external pressure, the drug solution in the body portion may enter a gap between a female luer section positioned closer to a distal end than the proximal end section of the cylindrical portion and the cap, and may adhere to the inner peripheral surface of the female luer section.

When a male luer section of another medical device (e.g., a syringe) is inserted into the female luer section with the drug solution adhering to the inner peripheral surface of the female luer section, the drug solution enters into a gap between the outer peripheral surface of the male luer section and the inner peripheral surface of the female luer section. In this state, the engagement between the female luer section and the male luer section may become loose, which may cause a leakage of the drug solution.

SUMMARY

In accordance with an aspect, a syringe and a prefilled syringe are disclosed that can help prevent a drug solution from adhering to the inner peripheral surface of a female luer section, and can help prevent a leakage of the solution in a state where a male luer section is engaged with the female luer section.

In accordance with another aspect, a syringe according to the present disclosure includes: a barrel body including a body portion that is hollow and that is capable of being filled with a drug solution, and a cylindrical portion that protrudes in a distal direction from a distal end of the body portion and includes an opening open at a distal end of the cylindrical portion, the cylindrical portion defining a flow path that connects an inside of the body portion and the opening; and a cap including a cap body that is attached to the cylindrical portion and that is made of an elastic material, in which the cylindrical portion includes a female luer section that has an inner diameter reduced in a proximal direction from the opening and that is engageable with a male luer section of another medical device, and a proximal end section that connects the female luer section and the body portion, the cap body includes a base located closer to the distal end than the opening in a state where the cap body is attached to the cylindrical portion, and an insertion portion that protrudes from the base in a proximal direction and that is to be inserted into the cylindrical portion, the insertion portion of the cap body includes a first sealing section that is provided at a distal end of the insertion portion and that has an outer diameter greater than a diameter of the opening in a natural state where the cap body is not attached to the cylindrical portion, and a second sealing section that is provided at a proximal end of the insertion portion and that has an outer diameter greater than an inner diameter of the proximal end section of the cylindrical portion in the natural state, and when the cap body is attached to the cylindrical portion, the first sealing section seals a distal end section of the flow path in a liquid-tight manner by being compressed radially inward by an inner peripheral surface constituting the opening of the cylindrical portion, and the second sealing section seals a proximal end section of the flow path in a liquid-tight manner by being compressed radially inward by an inner peripheral surface of the proximal end section of the cylindrical portion.

In accordance with an aspect, the second sealing section of the cap body seals the proximal end section of the flow path of the cylindrical portion in a liquid-tight manner, whereby the drug solution in the barrel body can be prevented from entering into the cylindrical portion. Thus, adherence of the drug solution to the inner peripheral surface of the female luer section can be prevented. Accordingly, when a male luer section of another medical device is inserted into the female luer section, loosening of engagement between the female luer section and the male luer section can be prevented. As a result, a leakage of the solution in the state where the male luer section is engaged with the female luer section can be prevented. In addition, the first sealing section of the cap body seals the distal end section of the flow path of the cylindrical portion in a liquid-tight manner, whereby intrusion of bacteria into the barrel body from outside can be prevented.

In the syringe described above, the cap body may have a proximal-end protruding portion protruding in the proximal direction from the insertion portion, and when the cap body is attached to the cylindrical portion, the proximal-end protruding portion may be disposed within a distal end section of the body portion.

Meanwhile, when the drug solution enters the cylindrical portion having a smaller inner diameter than the body portion during, for example, a freeze-drying process of the drug solution in the syringe, the drug solution within the cylindrical portion may not be effectively freeze-dried, because the thermal conductivity and drying efficiency are different between the cylindrical portion and the body portion. According to the configuration described above, the drug solution in the body portion can be reliably prevented from entering the cylindrical portion by the proximal-end protruding portion, so that the drug solution can be freeze-dried rather effectively.

In the syringe described above, the proximal-end protruding portion may be formed to protrude toward a proximal end in a tapered manner.

According to such a configuration, the internal pressure of the body portion can be distributed in a direction intersecting with the axial direction of the cap body, whereby, even if the internal pressure of the body portion increases, detachment of the cap body from the cylindrical portion can be prevented.

In the syringe described above, the proximal end section of the cylindrical portion may include an annular protruding section that is formed such that the inner peripheral surface of the proximal end section protrudes radially inward and that compresses the second sealing section radially inward, the cap body may include an expanded portion on a proximal end of the second sealing section, the expanded portion having an outer diameter greater than that of the second sealing section, and when the cap body is attached to the cylindrical portion, a distal end of the expanded portion may be engaged with a proximal end of the annular protruding section.

According to such a configuration, the distal end of the expanded portion engages with the proximal end of the annular protruding section, which can prevent the cap body from dropping from the cylindrical portion.

In the syringe described above, the proximal end section of the cylindrical portion may have an annular recess formed such that the inner peripheral surface of the proximal end section is recessed radially outward, the second sealing section may have an outer diameter greater than an inner diameter of the annular recess, the insertion portion may have a reduced portion at a distal end of the second sealing section, the reduced portion having an outer diameter smaller than that of the second sealing section, and when the cap body is attached to the cylindrical portion, the second sealing section may be compressed radially inward by the annular recess, and the distal end of the second sealing section may be engaged with a distal end of the annular recess.

According to such a configuration, the distal end of the second sealing section engages with the distal end of the annular recess, which can help prevent the cap body from dropping from the cylindrical portion.

In the syringe described above, the cap body may include, between the first sealing section and the second sealing section, an intermediate section having an outer diameter smaller than an inner diameter of the female luer section.

According to such a configuration, the intermediate section is not compressed by the female luer section when the cap body is attached to the cylindrical portion. Therefore, the cap body can be prevented from being tightly fitted into the cylindrical portion, whereby the cap body can be removed rather easily from the cylindrical portion.

In the syringe described above, the cap body may include, between the intermediate section and the second sealing section, a third sealing section having an outer diameter greater than an inner diameter of the cylindrical portion in the natural state, and the third sealing section may seal the flow path in a liquid-tight manner by being compressed radially inward by the inner peripheral surface of the cylindrical portion.

According to such a configuration, it is possible to reliably prevent the drug solution from entering the female luer section while preventing the cap body from being tightly fitted into the cylindrical portion.

In the syringe described above, the cap may further include a cover member that is cylindrical, the cover member being made of a material harder than the cap body and having an engagement portion to be engaged with the base of the cap body, and the cover member may be attached to the cap body so as to cover at least a part of an outer peripheral surface of the base due to an engagement between the engagement portion and the base.

According to such a configuration, the cover member made of a relatively hard material, which functions as a grip, and whereby the cap body can be rather easily removed from the cylindrical portion.

In the syringe described above, the cover member may include a first cover portion that is cylindrical, the first cover portion having the engagement portion and covering the outer peripheral surface of the base, and a second cover portion that extends in a proximal direction from the first cover portion and that covers an outer peripheral surface of the cylindrical portion.

According to such a configuration, the second cover portion covers the outer peripheral surface of the cylindrical portion, and thus, it is possible to prevent the cylindrical portion from being damaged, for example, by an impact during transportation or storage of the syringe.

In the syringe described above, the second cover portion may have a female screw section on an inner peripheral surface, and the cylindrical portion may have a screw portion that is screwed to the female screw section on the outer peripheral surface.

According to such a configuration, when the cover member is rotated with respect to the cylindrical portion to remove the cap body from the cylindrical portion, the movement speed of the cap body in the axial direction can be limited. Therefore, when the cap body is removed from the cylindrical portion, the drug solution (drug) in the body portion can be prevented from scattering (or leaking) to the outside.

In the syringe described above: the cover member may include a cover main body that has the engagement portion and that has an opening on a distal end of the cover member, the cover main body being made of a substantially opaque material, and a distal-end cover member attached to the opening of the cover main body; the distal-end cover member may include an annular peripheral wall extending in a distal direction from the opening of the cover main body, a distal-end wall provided on a distal end of the annular peripheral wall, and a receiving space defined by the annular peripheral wall and the distal-end wall and capable of receiving at least a part of the base; the annular peripheral wall may have a view allowing portion for allowing an inside of the receiving space to be visible; the insertion portion of the cap body may have a contact portion located closer to a proximal end than the first sealing section and having an outer diameter greater than an inner diameter of the opening of the cylindrical portion; the cap body may be displaceable along an axial direction of the cover member within the cover member from a first position where the base is located within the cover main body to a second position where at least a part of the base protrudes into the receiving space from the opening of the cover main body; the engagement portion may be engageable with the base of the cap body so as to allow movement of the cap body with respect to the cover member in a distal direction, while preventing detachment of the cap body from the cover member in a proximal direction; the distal-end wall may be contactable to a distal end of the cap body so as to prevent detachment of the cap body from the cover member in the distal direction; the first sealing section may seal the distal end section of the flow path in a liquid-tight manner, and the second sealing section may seal the proximal end section of the flow path in a liquid-tight manner, in a state where the cap body is located in the first position; and the cap body in the first position may displace to the second position so that an outer periphery of the base is visible through the view allowing portion of the annular peripheral wall, due to a contact between the contact portion of the insertion portion and a distal end section of the cylindrical portion.

According to such a configuration, the cap body displaces to the second position from the first position where the cap body is covered by the substantially opaque cover main body, by which the outer periphery of the base of the cap body is visible through the view allowing portion. Thus, even when the cap body once removed from the cylindrical portion is reattached to the cylindrical portion (recapped), a user can rather easily and reliably identify whether the cap is unopened or whether the cap is opened.

In the syringe described above, the view allowing portion may include a transparent portion formed in at least a part of the annular peripheral wall.

The configuration described above can help ensure that the cap body is visible through the view allowing portion.

In the syringe described above, the distal-end cover member may be made of a transparent material, and the annular peripheral wall may entirely serve as the view allowing portion.

According to such a configuration, the cap body is visible through the view allowing portion with a simple configuration.

A prefilled syringe according to the present disclosure includes: the syringe described above; a drug solution filled in the body portion; and a gasket that is slidable in an axial direction within the body portion in a liquid-tight manner.

According to such a configuration, a prefilled syringe having an effect similar to the effect of the abovementioned syringe can be obtained.

According to the present disclosure, since the second sealing section of the cap body seals the proximal end section of the flow path of the cylindrical portion in a liquid-tight manner, adherence of the drug solution to the inner peripheral surface of the female luer section can be prevented, whereby leakage of the solution in a state where the male luer section is engaged with the female luer section can be prevented.

In accordance with an aspect, a syringe is disclosed, the syringe comprising: a barrel body including a body portion that is hollow and configured to be filled with a drug solution, and a cylindrical portion that protrudes in a distal direction from a distal end of the body portion and includes an opening at a distal end of the cylindrical portion, the cylindrical portion defining a flow path that connects an inside of the body portion and the opening; a cap including a cap body that is attached to the cylindrical portion, the cap body being made of an elastic material, the cylindrical portion includes a female luer section having an inner diameter reduced in a proximal direction from the opening and configured to be engageable with a male luer section of another medical device, and a proximal end section that connects the female luer section and the body portion; the cap body includes a base located closer to the distal end than the opening in a state where the cap body is attached to the cylindrical portion, and an insertion portion that protrudes from the base in a proximal direction and configured to be inserted into the cylindrical portion; the insertion portion of the cap body includes a first sealing section provided at a distal end of the insertion portion and having an outer diameter greater than a diameter of the opening in a natural state where the cap body is not attached to the cylindrical portion, and a second sealing section provided at a proximal end of the insertion portion and having an outer diameter greater than an inner diameter of the proximal end section of the cylindrical portion in the natural state; and when the cap body is attached to the cylindrical portion, the first sealing section seals a distal end section of the flow path in a liquid-tight manner by being compressed radially inward by an inner peripheral surface constituting the opening of the cylindrical portion, and the second sealing section seals a proximal end section of the flow path in a liquid-tight manner by being compressed radially inward by an inner peripheral surface of the proximal end section of the cylindrical portion.

In accordance with another aspect, a prefilled syringe is disclosed, the prefilled syringe comprising: a syringe, the syringe comprising a barrel body including a body portion that is hollow and configured to be filled with a drug solution, and a cylindrical portion that protrudes in a distal direction from a distal end of the body portion and includes an opening at a distal end of the cylindrical portion, the cylindrical portion defining a flow path that connects an inside of the body portion and the opening, a cap including a cap body that is attached to the cylindrical portion, the cap body being made of an elastic material, the cylindrical portion includes a female luer section having an inner diameter reduced in a proximal direction from the opening and configured to be engageable with a male luer section of another medical device, and a proximal end section that connects the female luer section and the body portion, the cap body includes a base located closer to the distal end than the opening in a state where the cap body is attached to the cylindrical portion, and an insertion portion that protrudes from the base in a proximal direction and configured to be inserted into the cylindrical portion, the insertion portion of the cap body includes a first sealing section provided at a distal end of the insertion portion and having an outer diameter greater than a diameter of the opening in a natural state where the cap body is not attached to the cylindrical portion, and a second sealing section provided at a proximal end of the insertion portion and having an outer diameter greater than an inner diameter of the proximal end section of the cylindrical portion in the natural state, and when the cap body is attached to the cylindrical portion, the first sealing section seals a distal end section of the flow path in a liquid-tight manner by being compressed radially inward by an inner peripheral surface constituting the opening of the cylindrical portion, and the second sealing section seals a proximal end section of the flow path in a liquid-tight manner by being compressed radially inward by an inner peripheral surface of the proximal end section of the cylindrical portion; a drug solution filled in the body portion; and a gasket that is slidable in an axial direction within the body portion in a liquid-tight manner.

In accordance with an aspect, a syringe is disclosed, the syringe comprising: a barrel body including a hollow body portion and a cylindrical portion that protrudes in a distal direction from a distal end of the body portion and includes an opening at a distal end of the cylindrical portion, the cylindrical portion defining a flow path that connects an inside of the body portion and the opening; a cap including a cap body that is attached to the cylindrical portion, the cylindrical portion includes a female luer section having an inner diameter reduced in a proximal direction from the opening and configured to be engageable with a male luer section of another medical device, and a proximal end section that connects the female luer section and the body portion; the cap body includes a base located closer to the distal end than the opening in a state where the cap body is attached to the cylindrical portion, and an insertion portion that protrudes from the base in a proximal direction and configured to be inserted into a cylindrical portion; the insertion portion of the cap body includes a first sealing section provided at a distal end of the insertion portion and having an outer diameter greater than a diameter of the opening in a natural state where the cap body is not attached to the cylindrical portion, and a second sealing section provided at a proximal end of the insertion portion and having an outer diameter greater than an inner diameter of the proximal end section of the cylindrical portion in the natural state; when the cap body is attached to the cylindrical portion, the first sealing section seals a distal end section of the flow path in a liquid-tight manner by being compressed radially inward by an inner peripheral surface constituting the opening of the cylindrical portion, and the second sealing section seals a proximal end section of the flow path in a liquid-tight manner by being compressed radially inward by an inner peripheral surface of the proximal end section of the cylindrical portion; and a cylindrical cover member, the cylindrical cover member including an engagement portion configured to be engaged with the base of the cap body, and wherein the cover member is configured to be attachable to the cap body so as to cover at least a part of an outer peripheral surface of the base due to an engagement between the engagement portion and the base.

BRIEF DESCRIPTION OF THE DRAWINGS

FIG. 2A is an exploded longitudinal sectional view of a distal end section of the syringe in FIG. 1.

FIG. 2B is a longitudinal sectional view of a distal end section of the prefilled syringe in FIG. 1.

FIG. 3 is an exploded perspective view of the distal end section of the prefilled syringe in FIG. 1.

FIG. 6A is an exploded longitudinal sectional view of a distal end section of a syringe provided with a cap body according to a third modification.

FIG. 6B is a longitudinal sectional view of a distal end section of a prefilled syringe in which the cap body in FIG. 6A is attached to a cylindrical portion.

FIG. 7 is a longitudinal sectional view of a distal end section of a prefilled syringe according to a second embodiment disclosed here.

FIG. 11 is an exploded perspective view of the distal end section of the prefilled syringe in FIG. 10.

FIG. 12A is a longitudinal sectional view showing a state where a cap is removed from a cylindrical portion in FIG. 10.

FIG. 12B is a longitudinal sectional view showing a state where the cap is recapped on the cylindrical portion.

DETAILED DESCRIPTION

Set forth below with reference to the accompanying drawings is a detailed description of embodiments of a syringe and a prefilled syringe representing examples of the inventive of the syringe and the prefilled syringe disclosed here.

First Embodiment

Figure 1:
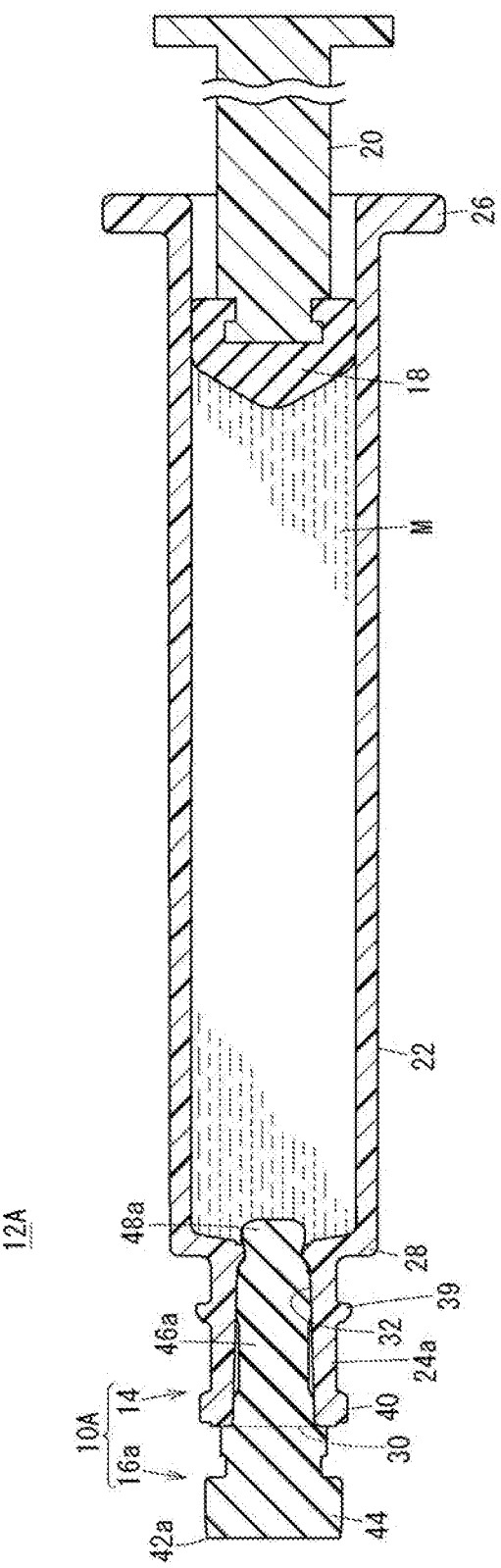
FIG. 1 is a longitudinal sectional view of a prefilled syringe according to a first embodiment disclosed here.

As shown in FIG. 1, a prefilled syringe 12A includes a syringe 10A having a barrel body 14 and a cap 16a, a drug solution M (drug) filled in the barrel body 14, a gasket 18 which is inserted into the barrel body 14 in a slidable manner, and a pusher 20 connected to the gasket 18.

The barrel body 14 has a hollow body portion 22 which can be filled with the drug solution M, a cylindrical portion 24a protruding in a distal direction from a distal end section of the body portion 22, and a flange 26 provided at a proximal end section of the body portion 22. The body portion 22, the cylindrical portion 24a, and the flange 26 are integrally formed.

The barrel body 14 material is not particularly limited, and examples of the material of the barrel body 14 can include: a resin material including polyolefin such as polypropylene, polyurethane, polyethylene, cyclic polyolefin, or polymethylpentene 1, polyester, nylon, polycarbonate, polymethyl methacrylate (PMMA), polyether imide (PEI), polyethersulfone, polyether ether ketone (PEEK), fluororesin, polyphenylene sulfide (PPS), or polyacetal resin (POM); a metal material such as stainless; and glass.

Figure 4:
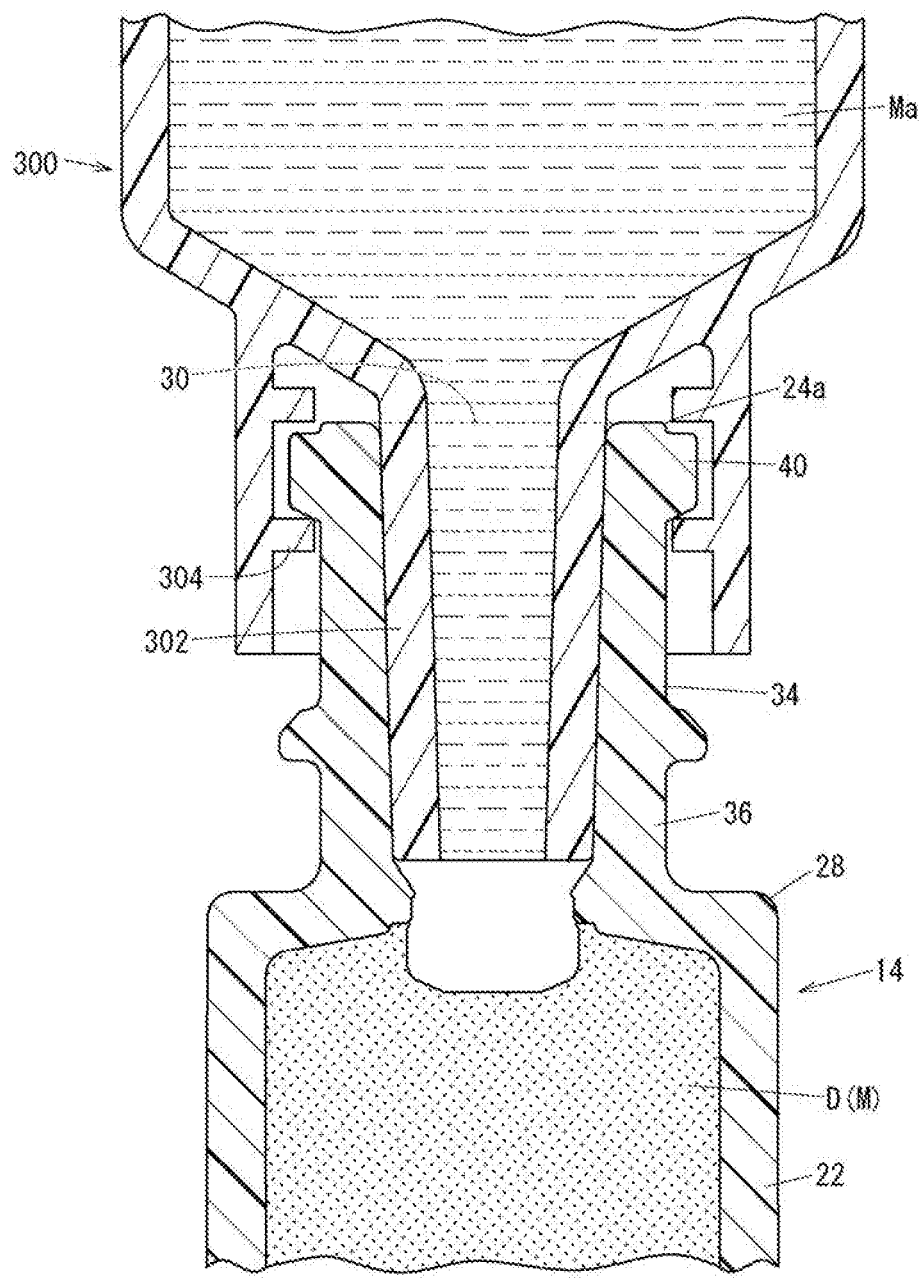
FIG. 4 is a longitudinal sectional view, a part of which is omitted, showing a state in which a male luer section of another medical device is engaged with a female luer section of the syringe in FIG. 1.

The body portion 22 is formed into a cylindrical shape and extends in an axial direction. A shoulder 28 whose diameter is reduced toward the proximal end of the cylindrical portion 24a is formed at the distal end section of the body portion 22. As shown in FIG. 2A, the cylindrical portion 24a has an opening 30 that is open at the distal end, and defines a flow path 32 that connects the inside of the body portion 22 and the opening 30. In FIG. 4, the cylindrical portion 24a has an inner diameter reduced in a proximal direction from the opening 30, and includes a female luer section 34 that can be engaged with a male luer section 302 of another medical device 300 (another syringe) and a proximal end section 36 that connects the female luer section 34 and the body portion 22 to each other.

As shown in FIGS. 2A and 2B, the proximal end section 36 of the cylindrical portion 24a has an annular protruding section 38 formed such that the inner peripheral surface of the proximal end section 36 protrudes radially inward. The annular protruding section 38 compresses radially inward onto a later-described second sealing section 58a which constitutes the cap 16a. In FIGS. 2A, 2B, and 3, an annular protrusion 39 is provided on the outer peripheral surface of the proximal end section 36 of the cylindrical portion 24a. A male screw section 40 (screw section) to be screwed to a female screw section 304 (see FIG. 4) of another medical device 300 is provided on the outer peripheral surface of the cylindrical portion 24a.

In FIG. 1, the gasket 18 is slidable in the axial direction within the barrel body 14 in a liquid-tight manner, and delivers the drug solution M filled in the barrel body 14. The tip of the pusher 20 can be connected to the gasket 18.

As shown in FIGS. 2A, 2B, and 3, the cap 16a has a cap body 42a which is made of an elastic material and which is attached to the cylindrical portion 24a. In accordance with an aspect, rubber or a synthetic resin elastomer may be used as a material constituting the cap body 42a. Examples of usable rubber can include, for example, isoprene rubber, butyl rubber, latex rubber, and silicone rubber. Examples of usable synthetic resin elastomer can include, for example, a styrene elastomer and an olefin elastomer.

The cap body 42a has a base 44 which is located closer to the distal end than the opening 30 in a state where the cap body 42a is attached to the cylindrical portion 24a, an insertion portion 46a which protrudes in the proximal direction from the base 44 and which is to be inserted into the cylindrical portion 24a, and a proximal-end protruding portion 48a which protrudes in the proximal direction from the insertion portion 46a.

The base 44 has a base body 50 which is columnar and which defines a portion of the cap body 42a having the maximum outer diameter of the cap body 42a, a small-diameter intermediate section 52 provided on the proximal end surface of the base body 50, and a large-diameter intermediate section 54 provided on the proximal end surface of the small-diameter intermediate section 52. The outer diameter of the small-diameter intermediate section 52 is smaller than the outer diameter of the large-diameter intermediate section 54. The outer diameter of the large-diameter intermediate section 54 is greater than the diameter of the opening 30 of the cylindrical portion 24a. When the cap body 42a is attached to the cylindrical portion 24a, the proximal end surface of the large-diameter intermediate section 54 is in contact with the distal end surface of the cylindrical portion 24a. It is to be noted, however, that the proximal end surface of the large-diameter intermediate section 54 may be in proximity to the distal end surface of the cylindrical portion 24a, when the cap body 42a is attached to the cylindrical portion 24a.

The insertion portion 46a includes a first sealing section 56, a second sealing section 58a, an intermediate section 60, and a third sealing section 62. The first sealing section 56 is provided on the proximal end surface of the large-diameter intermediate section 54. In a natural state in which the cap body 42a is not attached to the cylindrical portion 24a, the first sealing section 56 is provided at the distal end of the insertion portion 46a and has an outer diameter greater than the diameter of the opening 30. When the cap body 42a is attached to the cylindrical portion 24a, the first sealing section 56 is compressed radially inward by the inner peripheral surface that defines the opening 30 of the cylindrical portion 24a, thereby sealing the distal end section of the flow path 32 in a liquid-tight manner (see FIG. 2B).

In the natural state, the second sealing section 58a is provided at the proximal end of the insertion portion 46a, and has an outer diameter greater than the inner diameter of the proximal end section 36 (annular protruding section 38) of the cylindrical portion 24a. When the cap body 42a is attached to the cylindrical portion 24a, the second sealing section 58a is compressed radially inward by the inner peripheral surface of the proximal end section 36 (annular protruding section 38) of the cylindrical portion 24a, thereby sealing the proximal end section of the flow path 32 in a liquid-tight manner.

The intermediate section 60 is provided between the first sealing section 56 and the second sealing section 58a, and has a constant outer diameter over the entire length of the intermediate section 60. The outer diameter of the intermediate section 60 is smaller than the minimum inner diameter of the female luer section 34. In other words, when the cap body 42a is attached to the cylindrical portion 24a, a predetermined gap S is formed between the intermediate section 60 and the female luer section 34 (see FIG. 2B).

The third sealing section 62 is provided between the intermediate section 60 and the second sealing section 58a, and has an outer diameter greater than the inner diameter of the proximal end section 36 (annular protruding section 38) of the cylindrical portion 24a in the natural state. When the cap body 42a is attached to the cylindrical portion 24a, the third sealing section 62 is compressed radially inward by the inner peripheral surface of the cylindrical portion 24a, thereby sealing the flow path 32 in a liquid-tight manner (see FIG. 2B). The third sealing section 62 is a portion having the maximum outer diameter of the insertion portion 46a.

When the cap body 42a is attached to the cylindrical portion 24a, the proximal-end protruding portion 48a is disposed within the distal end section of the body portion 22 (see FIG. 2B). The cap body 42a has an expanded portion 64 having an outer diameter greater than that of the second sealing section 58a on the proximal end side of the second sealing section 58a. When the cap body 42a is attached to the cylindrical portion 24a, the distal end of the expanded portion 64 engages with the proximal end of the annular protruding section 38. The proximal end surface of the proximal-end protruding portion 48a is a relatively flat surface.

Next, the operation of the prefilled syringe 12A according to the present embodiment configured as described above will be described.

In the present embodiment, the drug solution M filled in the body portion 22 of the prefilled syringe 12A shown in FIG. 1 can be freeze-dried. Thereafter, the cap body 42a is removed from the cylindrical portion 24a, and then, as shown in FIG. 4, the male screw section 40 of the cylindrical portion 24a is threaded into the female screw section 304 of the other medical device 300, whereby the male luer section 302 of the other medical device 300 is engaged with the female luer section 34 of the cylindrical portion 24a. At this time, the outer peripheral surface of the male luer section 302 contacts the inner peripheral surface of the female luer section 34. Then, a drug solution Ma filled in the other medical device 300 and the dry powder drug D (freeze-dried drug solution M) are mixed with each other, and the dry powder drug D is dissolved into the drug solution Ma. Thus, a desired drug solution is obtained.

It is to be noted that, in the present embodiment, a desired drug solution may be obtained by mixing the drug solution M in the prefilled syringe 12A that has not been freeze-dried with the drug solution Ma in the medical device 300.

In this case, the prefilled syringe 12A according to the present embodiment has the following effects.

When the cap body 42a is attached to the cylindrical portion 24a, the second sealing section 58a of the cap body 42a is compressed radially inward by the inner peripheral surface of the proximal end section 36 of the cylindrical portion 24a, thereby sealing the proximal end section of the flow path 32 of the cylindrical portion 24a in a liquid-tight manner. Therefore, the drug solution M in the barrel body 14 can be prevented from entering the cylindrical portion 24a. Thus, adherence of the drug solution M to the inner peripheral surface of the female luer section 34 can be prevented.

Accordingly, the engagement between the female luer section 34 and the male luer section 302 can be prevented from becoming loose when the male luer section 302 of the other medical device 300 is inserted into the female luer section 34. As a result, a leakage of the solution in the state where the male luer section 302 is engaged with the female luer section 34 can be prevented.

In addition, the first sealing section 56 provided at the distal end of the insertion portion 46a of the cap body 42a is compressed radially inward by the inner peripheral surface that defines the opening 30 of the cylindrical portion 24a, thereby sealing the distal end section of the flow path 32 of the cylindrical portion 24a in a liquid-tight manner. Therefore, intrusion of bacteria into the barrel body 14 from the outside can be prevented.

Meanwhile, when the drug solution M enters the cylindrical portion 24a having a smaller inner diameter than the body portion 22 during a freeze-drying process of the drug solution M in the syringe 10A, the drug solution M within the cylindrical portion 24a may not be effectively freeze-dried, because the thermal conductivity and drying efficiency are different between the cylindrical portion 24a and the body portion 22.

In accordance with an aspect, the cap body 42a has the proximal-end protruding portion 48a protruding in the proximal direction from the insertion portion 46a, and when the cap body 42a is attached to the cylindrical portion 24a, the proximal-end protruding portion 48a is located within the distal end section of the body portion 22. This configuration can reliably prevent the drug solution M in the body portion 22 from entering the cylindrical portion 24a by the proximal-end protruding portion 48a, so that the drug solution M can be freeze-dried effectively.

The proximal end section 36 of the cylindrical portion 24a has the annular protruding section 38 which is formed such that the inner peripheral surface of the proximal end section 36 protrudes radially inward, the annular protruding section 38 compressing the second sealing section 58a radially inward. The cap body 42a has the expanded portion 64 having the outer diameter greater than that of the second sealing section 58a on the proximal end side of the second sealing section 58a. When the cap body 42a is attached to the cylindrical portion 24a, the distal end of the expanded portion 64 is engaged with the proximal end of the annular protruding section 38, which can help prevent the cap body 42a from disengaging (or dropping) from the cylindrical portion 24a.

The cap body 42a has the intermediate section 60 having an outer diameter smaller than the inner diameter of the female luer section 34 between the first sealing section 56 and the second sealing section 58a. With this configuration, when the cap body 42a is attached to the cylindrical portion 24a, the intermediate section 60 is not compressed by the female luer section 34. Therefore, it is possible to prevent the cap body 42a from being tightly fitted into the cylindrical portion 24a, whereby the cap body 42a can be rather easily removed from the cylindrical portion 24a.

The cap body 42a has, between the intermediate section 60 and the second sealing section 58a, the third sealing section 62 having an outer diameter greater than the inner diameter of the cylindrical portion 24a in the natural state. The third sealing section 62 is compressed radially inward by the inner peripheral surface of the cylindrical portion 24a, thereby sealing the flow path 32 of the cylindrical portion 24a in a liquid-tight manner. Accordingly, it is possible to reliably prevent the drug solution M from entering the female luer section 34 while preventing the cap body 42a from being tightly fitted into the cylindrical portion 24a.

Figure 5A:
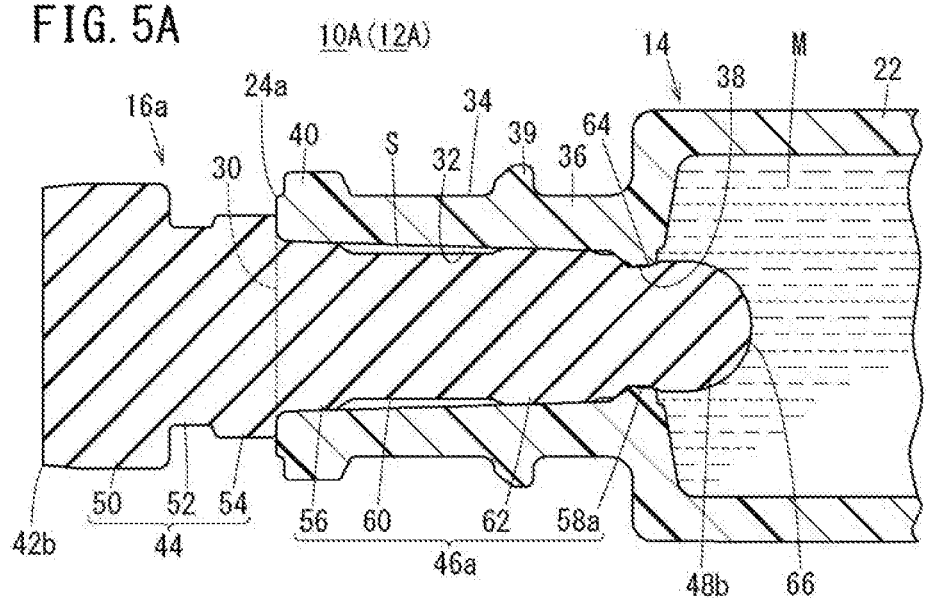
FIG. 5A is a longitudinal sectional view of a distal end section of a prefilled syringe provided with a cap body according to a first modification.

The cap 16a is not limited to have the configuration described above. As shown in FIG. 5A, a cap body 42b constituting the cap 16a may have a proximal-end protruding portion 48b that protrudes toward the proximal end in a tapered manner. The proximal-end protruding portion 48b is formed in a substantially hemispherical shape. That is, the outer surface of the proximal-end protruding portion 48b has a curved surface 66.

According to the cap 16a described above, the internal pressure of the body portion 22 can be distributed in a direction intersecting with the axial direction of the cap body 42b, whereby, even if the internal pressure of the body portion 22 increases, detachment of the cap body 42b from the cylindrical portion 24a can be prevented.

Figure 5B:
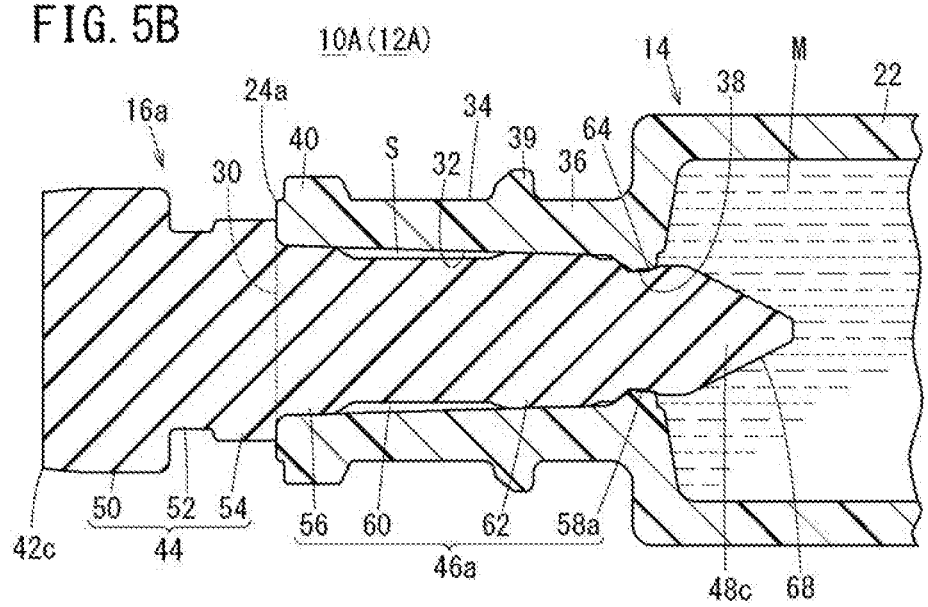
FIG. 5B is a longitudinal sectional view of a distal end section of a prefilled syringe provided with a cap body according to a second modification.

As shown in FIG. 5B, a cap body 42c constituting the cap 16a may have a proximal-end protruding portion 48c that protrudes toward the proximal end in a tapered manner. The proximal-end protruding portion 48c is formed in a substantially frusto-conical shape. That is, the outer surface of the proximal-end protruding portion 48c has an inclined surface 68 inclined radially inward in the proximal direction. According to the cap body 42c described above, an effect similar to the effect of the cap body 42b shown in FIG. 5A can be obtained.

The proximal-end protruding portions 48b and 48c of the cap body 42b, 42c may have any shape as long as they are tapered in the proximal direction. The proximal-end protruding portion 48c may be formed into, for example, a substantially triangular based pyramid or a substantially truncated triangular based pyramid.

As shown in FIG. 6A, the proximal end section 36 of a cylindrical portion 24b constituting the barrel body 14 may have an annular recess 70 formed such that the inner peripheral surface of the proximal end section 36 is recessed radially outward, instead of the annular protruding section 38. In this case, a cap body 42d constituting the cap 16a has an insertion portion 46b which includes: a second sealing section 58b having an outer diameter greater than the inner diameter of the annular recess 70; and a proximal-end protruding portion 48d provided at the proximal end of the second sealing section 58b. The insertion portion 46b is provided with a reduced portion 74 having an outer diameter smaller than the outer diameter of the second sealing section 58b between the second sealing section 58b and the third sealing section 62. The second sealing section 58b is a portion having the maximum outer diameter of the insertion portion 46b. The proximal-end protruding portion 48d has a configuration similar to that of the proximal-end protruding portion 48c described above.

As shown in FIG. 6B, when the cap body 42d configured as described above is attached to the cylindrical portion 24b, the second sealing section 58b is compressed radially inward by the annular recess 70, and the distal end of the second sealing section 58b is engaged with the distal end of the annular recess 70.

According to such a configuration, the distal end of the second sealing section 58b engages with the distal end of the annular recess 70, which can prevent the cap body 42d from disengaging from the cylindrical portion 24b.

Second Embodiment

Next, a prefilled syringe 12B provided with a syringe 10B according to a second embodiment of the present disclosure will be described. In the prefilled syringe 12B according to the second embodiment, the same components as those described in the above embodiment are denoted by the same reference numerals, and the detailed description of the same components will be omitted. The same applies to a third embodiment described later.

Figure 8:
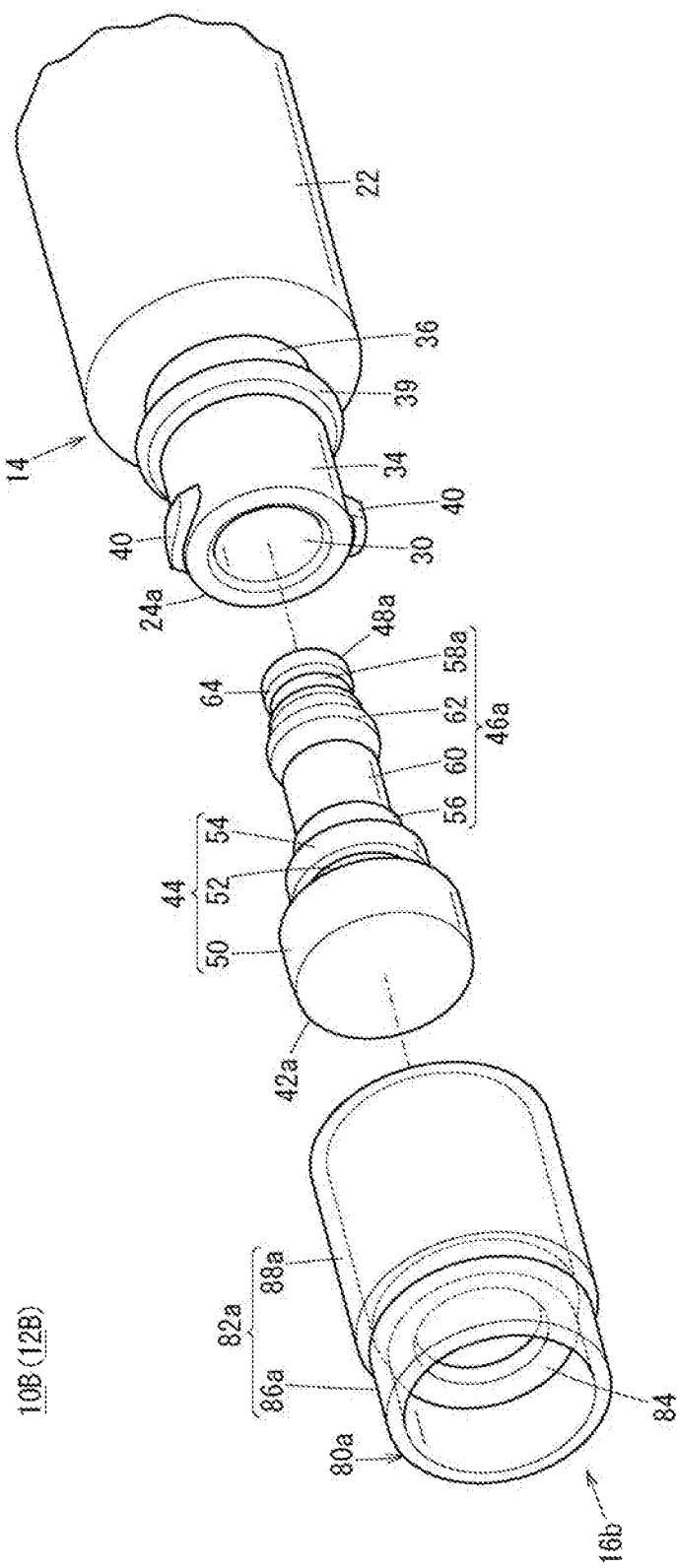
FIG. 8 is an exploded perspective view of the distal end section of the prefilled syringe in FIG. 7.

As shown in FIGS. 7 and 8, the syringe 10B constituting the prefilled syringe 12B includes a barrel body 14 and a cap 16*b*. The cap 16*b* has a cap body 42*a* and a cover member 80*a* that covers the cap body 42*a*.

The cover member 80*a* is made of a material (for example, a resin material) harder than the cap body 42*a*. The cover member 80*a* has a cylindrical main body 82*a* having a cylindrical shape, and an engagement portion 84 provided on the inner peripheral surface of the cylindrical main body 82*a*. The cylindrical main body 82*a* includes a cylindrical first cover portion 86*a* that covers a base 44, and a cylindrical second cover portion 88*a* that extends in the proximal direction from the proximal end of the first cover portion 86*a*.

The overall length of the first cover portion 86*a* is longer than the axial length of a base body 50. That is, the first cover portion 86*a* entirely covers the outer peripheral surface of the base body 50. However, the first cover portion 86*a* only needs to cover at least a part of the outer peripheral surface of the base body 50.

The second cover portion 88*a* covers the outer peripheral surface of the cylindrical portion 24*a* in a state where the cap body 42*a* is attached to the cylindrical portion 24*a*. The proximal end surface of the second cover portion 88*a* faces the shoulder 28 of the barrel body 14 with a gap between the proximal end surface of the second cover portion 88*a* and the shoulder 28 in a state where the cap body 42*a* is attached to the cylindrical portion 24*a*.

The engagement portion 84 is provided at a joint part between the first cover portion 86*a* and the second cover portion 88*a*, and engages with the base 44 of the cap body 42*a*. The engagement portion 84 protrudes radially inward from the inner surface of the cylindrical main body 82*a* and circumferentially extends along the entire circumference. That is, the engagement portion 84 is annularly formed. The protruding end of the engagement portion 84 is held between the base body 50 and the large-diameter intermediate section 54 (see FIG. 7). Accordingly, the movement of the cover member 80*a* in the axial direction with respect to the cap body 42*a* can be restricted.

In the prefilled syringe 12B configured as described above, a user can remove the cap body 42*a* from the cylindrical portion 24*a* by pulling the cap 16*b* in the distal direction from the barrel body 14 while holding the outer peripheral surface of the cover member 80*a*. Therefore, according to the prefilled syringe 12B, the cover member 80*a* made of a relatively hard material can function as a grip, whereby the cap body 42*a* can be rather easily removed from the cylindrical portion 24*a*.

Further, since the second cover portion 88*a* covers the outer peripheral surface of the cylindrical portion 24*a*, the cylindrical portion 24*a* can be prevented from being damaged by an impact during transportation or storage of the syringe 10B (prefilled syringe 12B).

Figure 9A:
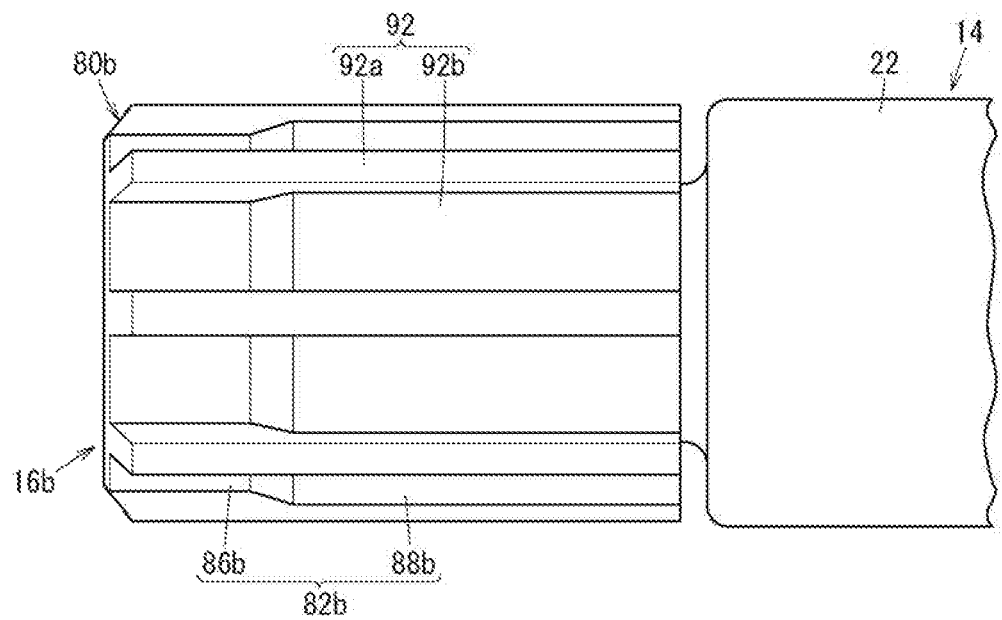
FIG. 9A is a plan view of a distal end section of a prefilled syringe provided with a cover member according to a modification.
Figure 9B:
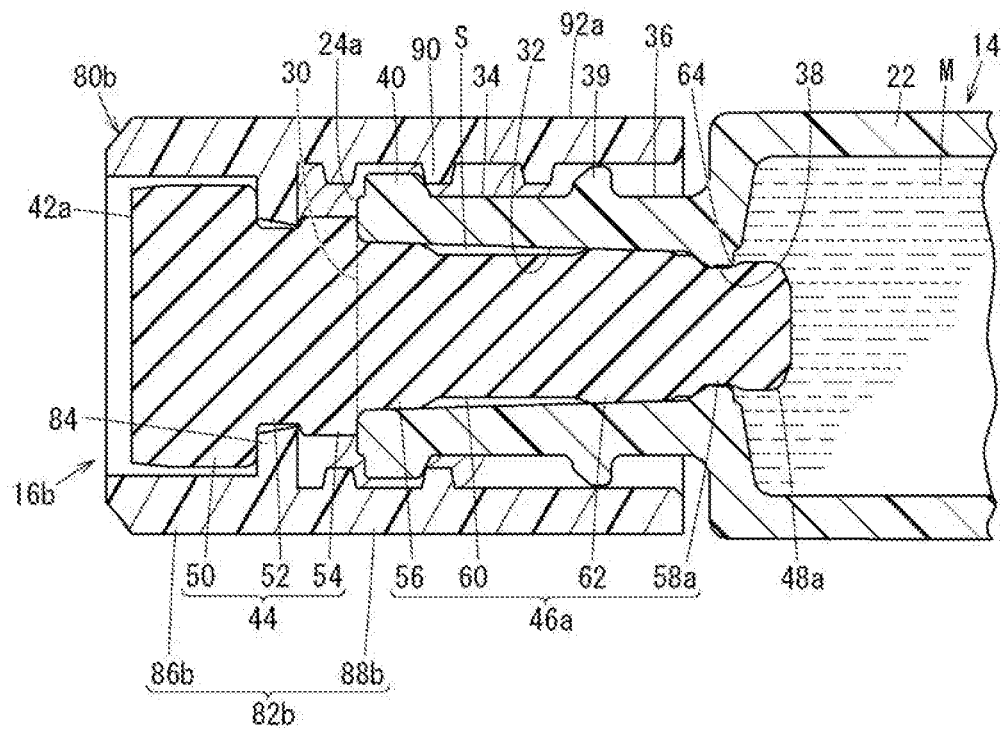
FIG. 9B is a longitudinal sectional view of the distal end section of the prefilled syringe shown in FIG. 9A.

The cap 16*b* may include a cover member 80*b* shown in FIGS. 9A and 9B instead of the cover member 80*a*. The cover member 80*b* has a cylindrical main body 82*b* and an engagement portion 84. As shown in FIG. 9B, the cylindrical main body 82*b* includes a cylindrical first cover portion 86*b* that covers the base 44, and a cylindrical second cover portion 88*b* that extends in the proximal direction from the proximal end of the first cover portion 86*b*. A female screw section 90 that is screwed to the male screw section 40 of the cylindrical portion 24*a* is formed on the inner peripheral surface of the second cover portion 88*b*.

In FIG. 9A, a non-slip portion 92 that functions to prevent a slip of a user's finger is formed on the outer surface of the cylindrical main body 82*b*. The non-slip portion 92 is formed by providing, in an alternate manner, a plurality of projections 92*a* and recesses 92*b* which extend along the axial direction of the cylindrical main body 82*b* in the circumferential direction. The projections 92*a* and the recesses 92*b* extend over the entire length of the cylindrical main body 82*b*.

The non-slip portion 92 is not limited to have the configuration in which the projections 92*a* and the recesses 92*b* extending in the axial direction of the cylindrical main body 82*b* are provided alternately in the circumferential direction of the cylindrical main body 82*b*. For example, a plurality of protrusions or the like protruding from the outer peripheral surface of the cylindrical main body 82*b* in the form of a column may be used.

According to the cap 16*b* shown in FIGS. 9A and 9B, when the cover member 80*b* is rotated with respect to the cylindrical portion 24*a* to remove the cap body 42*a* from the cylindrical portion 24*a*, the movement speed of the cap body 42*a* in the axial direction is limited. Therefore, when the cap body 42*a* is removed from the cylindrical portion 24*a*, the drug solution M (dry powder drug D) in the body portion 22 can be prevented from scattering to the outside.

The syringe 10B may include any one of the cap bodies 42*b* to 42*d* described above instead of the cap body 42*a*.

Third Embodiment

Next, a prefilled syringe 12C including a syringe 10C according to a third embodiment of the present disclosure will be described.

Figure 10:
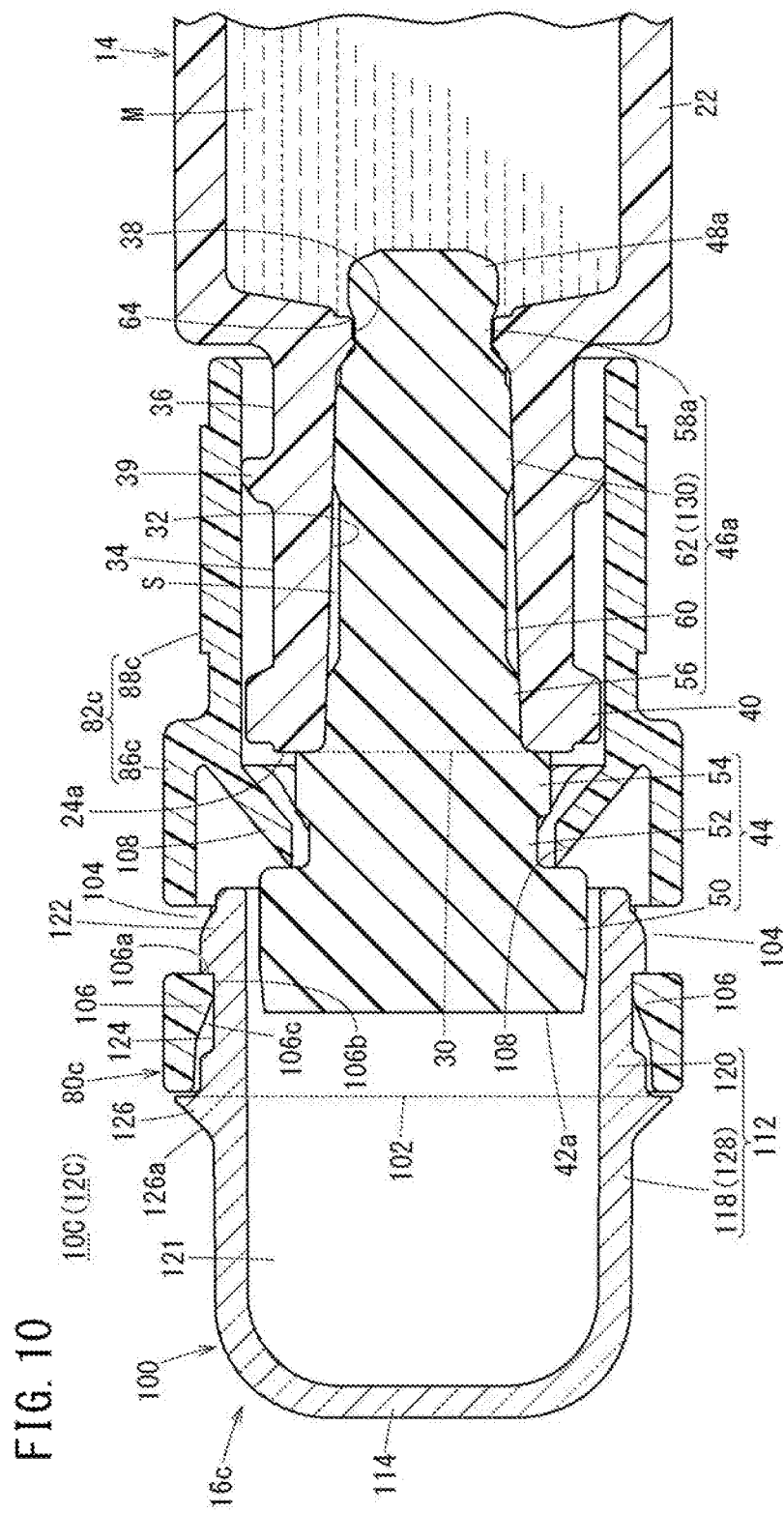
FIG. 10 is a longitudinal sectional view of a distal end section of a prefilled syringe according to a third embodiment disclosed here.

As shown in FIGS. 10 and 11, the syringe 10C constituting the prefilled syringe 12C includes a barrel body 14 and a cap 16*c*. The cap 16*c* has a cap body 42*a*, a cover member 80*c* that covers the cap body 42*a*, and a distal-end cover member 100 provided on the distal end side of the cover member 80*c*.

The cover member 80*c* is formed in a cylindrical shape, and is made of a resin material having no transparency (for example, a substantially opaque resin material). The cover member 80*c* has a cylindrical main body 82*c* that covers the cap body 42*a*. An opening 102 for exposing (projecting) the cap body 42*a* from the cylindrical main body 82*c* is formed at the distal end of the cylindrical main body 82*c*.

The cylindrical main body 82*c* has a cylindrical first cover portion 86*c* that covers the base 44, and a cylindrical second cover portion 88*c* that extends from the proximal end of the first cover portion 86*c* in the proximal direction. Two through holes 104 and two locking projections 106 for locking the distal-end cover member 100 are formed at the distal end section of the inner peripheral surface of the first cover portion 86*c*. In accordance with an aspect, the number of through holes 104 and the number of locking projections 106 instead of two, may be one or three or more, respectively.

Each through hole 104 is formed in a rectangular shape, and extends along the circumferential direction of the cylindrical main body 82*c*. These through holes 104 face each other. The length of each locking projection 106 along the circumferential direction is slightly shorter than the length of the through hole 104 along the circumferential direction. Each locking projection 106 has a first contact surface 106*a* continuous with a distal-side wall surface defining the through hole 104, a second contact surface 106*b* which extends from the first contact surface 106*a* in the distal direction so as to be parallel to the axis of the cylindrical main body 82*c*, and an inclined surface 106*c* which is inclined radially outward in the distal direction from the distal end of the second contact surface 106*b*.

The inner diameter of the second cover portion 88c is smaller than the inner diameter of the first cover portion 86c. The outer diameter of the second cover portion 88c is smaller than the outer diameter of the first cover portion 86c. The second cover portion 88c covers the outer surface of the cylindrical portion 24a in a state where the cap body 42a is attached to the cylindrical portion 24a. The inner surface of the second cover portion 88c contacts the protruding end surface of the annular protrusion 39.

Multiple (six in FIG. 11) engagement tabs 108 (engagement portions) which contact the proximal end surface (proximal stepped surface) of the base 44 are provided at the joint part between the first cover portion 86c and the second cover portion 88c at regular intervals in the circumferential direction of the cylindrical main body 82c. That is, a predetermined space is formed between the engagement tabs 108 that are adjacent to each other in the circumferential direction. Each engagement tab 108 extends in the distal direction from the inner surface of the cylindrical main body 82c so as to be inclined radially inward with respect to the axis of the cylindrical main body 82c, and is elastically deformable in the radial direction of the cylindrical main body 82c.

The diameter of a central hole 110 formed by the inner ends (tip surfaces) of the multiple engagement tabs 108 is smaller than the outer diameter of the base body 50. The engagement tabs 108 can be engaged with the base 44 of the cap body 42a so as to prevent detachment of the cap body 42a from the cover member 80c in the proximal direction while allowing the cap body 42a to move in the distal direction with respect to the cover member 80c.

The distal-end cover member 100 has a substantially U-shaped vertical cross section, and is attached to the opening 102 of the cover member 80c. The distal-end cover member 100 covers the cap body 42a so that a user manipulating the cap 16c together with the cover member 80c cannot touch the cap body 42a. That is, the distal-end cover member 100 has a contact preventing function. The distal-end cover member 100 also has a function as a detachment preventing portion that helps prevent the cap body 42a from being detached from the opening 102 of the cover member 80c.

In accordance with an aspect, the distal-end cover member 100 includes an annular portion 112 which has a proximal end section engaged with the distal end section of the cover member 80c such that the annular portion 112 extends in the distal direction from the opening 102 of the cylindrical main body 82c, and a distal-end wall 114 provided at the distal end of the annular portion 112. The inner diameter of the annular portion 112 is constant from the distal end to the proximal end, and the inner diameter of the annular portion 112 is greater than the outer diameter of the base 44.

The annular portion 112 includes an annular peripheral wall 118 on the distal end side, and a cylindrical engagement extending portion 120 extending from the proximal end of the annular peripheral wall 118 in the proximal direction. The annular peripheral wall 118 and the distal-end wall 114 define a receiving space 121 (see FIG. 10) that can receive at least a part of the base 44.

An annular locking tab 122 that contacts the first contact surfaces 106a of the locking projections 106 of the cover member 80c is provided in an area of the outer peripheral surface of the engagement extending portion 120 corresponding to the through holes 104 of the cover member 80c. The outer diameter of the locking tab 122 is greater than the distance between the locking projections 106.

An annular groove 124 into which the protruding ends of the locking projections 106 are inserted is formed on the outer peripheral surface of the engagement extending portion 120 on the distal end side of the locking tab 122. Second contact surfaces 106b which are protruding end surfaces of the locking projections 106 contact the bottom surface of the annular groove 124. Note that a wall surface of the annular groove 124 on the proximal end side is defined by the locking tab 122.

An annular positioning protrusion 126 that contacts with or is in proximity to the distal end surface of the cover member 80c is provided at the proximal end section of the outer peripheral surface of the annular peripheral wall 118. The positioning protrusion 126 has a triangular cross section. In other words, the positioning protrusion 126 has an inclined surface 126a that is inclined outward in the proximal direction on the distal end side. Accordingly, when the prefilled syringe 12C is inserted into an insertion tube or the like used for transporting the prefilled syringe 12C, the positioning protrusion 126 can be prevented from being caught on the edge of an opening of the insertion tube.

In accordance with an aspect, the distal-end cover member 100 is integrally formed using a transparent resin material. That is, the annular peripheral wall 118 serves as a view allowing portion 128 for allowing the inside of the receiving space 121 to be visible. In a case where the cover member 80c is made of a transparent resin material, the transparency of the distal-end cover member 100 is set higher than the transparency of the cover member 80c. Thus, the user can view the inside of the distal-end cover member 100 more clearly than the inside of the cover member 80c from the outside of the cap 16c. Although the distal-end cover member 100 is colorless in the present embodiment, it may be colored.

The distal-end wall 114 can contact the distal end of the cap body 42a so as to prevent the cap body 42a from being detached from the cover member 80c in the distal direction.

In the prefilled syringe 12C configured as described above, the base body 50 of the cap body 42a is located in a first position which is closer to the proximal end than the opening 102 of the cylindrical main body 82c in an unopened state of the cap 16c, as shown in FIG. 10. Specifically, the distal end of the cap body 42a is located closer to the proximal end than the opening 102 of the cylindrical main body 82c and within the engagement extending portion 120 of the distal-end cover member 100. Accordingly, the outer periphery of the base 44 is enclosed by the substantially opaque cylindrical main body 82c and is not visible from the outside. The insertion portion 46a is being attached to the cylindrical portion 24a, and therefore, the first sealing section 56 liquid-tightly seals the distal end section of the flow path 32 of the cylindrical portion 24a, the second sealing section 58a liquid-tightly seals the proximal end section of the flow path 32 of the cylindrical portion 24a, and the third sealing section 62 liquid-tightly seals the intermediate section 60 of the flow path 32 of the cylindrical portion 24a.

When the cap 16c is removed to open the barrel body 14, the cover member 80c is pulled out from the barrel body 14. Thus, as shown in FIG. 12A, the cap body 42a is pushed by the engagement tabs 108 in the distal direction, so that the insertion portion 46a is detached from the cylindrical portion 24a. As a result, the cap 16c is opened.

When the cap 16c which has been opened is reattached to the barrel body 14 (recapped), the distal end section of the cylindrical portion 24a is inserted into the second cover portion 88c from the opening on the proximal end side of the cylindrical main body 82c. Thus, as shown in FIG. 12B, the distal end section of the cylindrical portion 24a contacts the third sealing section 62 (contact portion 130) of the cap body 42a.

Subsequently, when the cover member 80c and the barrel body 14 are brought close to each other, the cap body 42a in the first position is pressed by the cylindrical portion 24a and displaces in the distal direction with respect to the cover member 80c due to the contact between the contact portion 130 of the cap body 42a and the distal end of the cylindrical portion 24a, so that the base 44 protrudes from the opening 102 on the distal end side of the cover member 80c in the distal direction.

Then, the proximal end of the cylindrical main body 82c approaches the shoulder 28 of the barrel body 14. Thus, the cap 16c which has been opened is reattached to the barrel body 14. At this time, the cap body 42a is located in the second position where the base 44 is received in the receiving space 121 formed by the annular peripheral wall 118 and the distal-end wall 114. Therefore, the outer periphery of the base 44 is visible from the outside through the view allowing portion 128 of the distal-end cover member 100.

According to the present embodiment, the cap body 42a displaces to the second position from the first position where the cap body 42a is covered by the substantially opaque cylindrical main body 82c, by which the outer periphery of the base 44 is visible through the view allowing portion 128. Thus, even when the cap body 42a once removed from the cylindrical portion 24a is reattached to the cylindrical portion 24a, the user can rather easily and reliably identify whether the cap 16c is unopened or opened.

The distal-end cover member 100 is made of a transparent material, and the whole of the annular peripheral wall 118 serves as the view allowing portion 128. Thus, the cap body 42a is visible through the view allowing portion 128 with a simple configuration.

In the syringe 10C, the view allowing portion 128 may be a transparent portion formed in at least a part of the annular peripheral wall 118. That is, the annular peripheral wall 118 may have a substantially opaque portion. Further, the view allowing portion 128 may be a window (opening) formed so as to penetrate the annular peripheral wall 118 constituting the distal-end cover member 100. These configurations can also help ensure that the cap body 42a is visible through the view allowing portion 128.

It is obvious that the syringe and the prefilled syringe according to the present disclosure are not limited to the abovementioned embodiments, and can employ various configurations without departing from the scope of the present disclosure.

The detailed description above describes embodiments of a syringe and a prefilled syringe in which a cap body made of an elastic material is attached to a cylindrical portion of a barrel body. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A syringe, the syringe comprising:
   a barrel body including a body portion that is hollow and configured to be filled with a drug solution, and a cylindrical portion that protrudes in a distal direction from a distal end of the body portion and includes an opening at a distal end of the cylindrical portion, the cylindrical portion defining a flow path that connects an inside of the body portion and the opening;
   a cap including a cap body that is configured to be attached to the cylindrical portion, the cylindrical portion includes a female luer section having an inner diameter reduced in a proximal direction from the opening and configured to be engageable with a male luer section of another medical device, and a proximal end section that connects the female luer section to the body portion;
   the cap body includes a base located closer to the distal end than the opening in a state where the cap body is attached to the cylindrical portion, and an insertion portion that protrudes from the base in a proximal direction and configured to be inserted into the cylindrical portion;
   the insertion portion of the cap body includes a first sealing section provided at a distal end of the insertion portion and having an outer diameter greater than a diameter of the opening in a natural state where the cap body is not attached to the cylindrical portion, and a second sealing section provided at a proximal end of the insertion portion and having an outer diameter greater than an inner diameter of the proximal end section of the cylindrical portion in the natural state;
   when the cap body is attached to the cylindrical portion, the first sealing section is configured to seal a distal end section of the flow path in a liquid-tight manner by being compressed radially inward by an inner peripheral surface constituting the opening of the cylindrical portion, and the second sealing section is configured to seal a proximal end section of the flow path in a liquid-tight manner by being compressed radially inward by an inner peripheral surface of the proximal end section of the cylindrical portion;
   the proximal end section of the cylindrical portion includes an annular protruding section, the inner peripheral surface of the proximal end section protruding radially inward and configured to compress the second sealing section radially inward;
   the cap body includes an expanded portion on a proximal end of the second sealing section, the expanded portion having an outer diameter greater than an outer diameter of the second sealing section; and
   when the cap body is attached to the cylindrical portion, a distal end of the expanded portion is configured to be engageable with a proximal end of the annular protruding section.

2. The syringe according to claim 1, wherein
   the cap body has a proximal-end protruding portion protruding in the proximal direction from the insertion portion; and
   when the cap body is attached to the cylindrical portion, the proximal-end protruding portion is configured to be disposed within a distal end section of the body portion.

3. The syringe according to claim 2, wherein the proximal-end protruding portion protrudes toward a proximal end in a tapered manner.

4. The syringe according to claim 1, wherein the cap body includes, between the first sealing section and the second sealing section, an intermediate section having an outer diameter smaller than an inner diameter of the female leer section.

5. The syringe according to claim 4, wherein the cap body includes, between the intermediate section and the second sealing section, a third sealing section having an outer diameter greater than an inner diameter of the cylindrical portion in the natural state, and the third sealing section configured to seal the flow path in a liquid-tight manner by being compressed radially inward by the inner peripheral surface of the cylindrical portion.

6. The syringe according to claim 1, wherein the cap further comprises:
   a cylindrical cover member, the cover member being made of a material harder than the cap body and having an engagement portion to be engaged with the base of the cap body; and
   the cover member is configured to be attachable to the cap body so as to cover at least a part of an outer peripheral surface of the base due to an engagement between the engagement portion and the base.

7. The syringe according to claim 6, wherein the cover member comprises:
   a cylindrical first cover portion, the first cover portion having the engagement portion and covering the outer peripheral surface of the base; and
   a second cover portion that extends in a proximal direction from the first cover portion and that covers an outer peripheral surface of the cylindrical portion.

8. The syringe according to claim 7, wherein the second cover portion has a female screw section on an inner peripheral surface, and the cylindrical portion has a screw portion that is screwed to the female screw section on the outer peripheral surface.

9. The syringe according to claim 1, wherein the cap body is made of an elastic material.

10. A syringe, the syringe comprising:
    a barrel body including a body portion that is hollow and configured to be filled with a drug solution, and a cylindrical portion that protrudes in a distal direction from a distal end of the body portion and includes an opening at a distal end of the cylindrical portion, the cylindrical portion defining a flow path that connects an inside of the body portion and the opening;
    a cap including a cap body that is configured to be attached to the cylindrical portion, the cylindrical portion includes a female luer section having an inner diameter reduced in a proximal direction from the opening and configured to be engageable with a male luer section of another medical device, and a proximal end section that connects the female luer section to the body portion;
    the cap body includes a base located closer to the distal end than the opening in a state where the cap body is attached to the cylindrical portion, and an insertion portion that protrudes from the base in a proximal direction and configured to be inserted into the cylindrical portion;
    the insertion portion of the cap body includes a first sealing section provided at a distal end of the insertion portion and having an outer diameter greater than a diameter of the opening in a natural state where the cap body is not attached to the cylindrical portion, and a second sealing section provided at a proximal end of the insertion portion and having an outer diameter greater than an inner diameter of the proximal end section of the cylindrical portion in the natural state;
    when the cap body is attached to the cylindrical portion, the first sealing section seals a distal end section of the flow path in a liquid-tight manner by being compressed radially inward by an inner peripheral surface constituting the opening of the cylindrical portion, and the second sealing section seals a proximal end section of the flow path in a liquid-tight manner by being compressed radially inward by an inner peripheral surface of the proximal end section of the cylindrical portion;
    the proximal end section of the cylindrical portion has an annular recess, the inner peripheral surface of the proximal end section being recessed radially outward;
    the second sealing section having an outer diameter greater than an inner diameter of the annular recess;
    the insertion portion having a reduced portion at a distal end of the second sealing section, the reduced portion having an outer diameter smaller than an outer diameter of the second sealing section; and
    when the cap body is attached to the cylindrical portion, the second sealing section is configured to be compressed radially inward by the annular recess, and the distal end of the second sealing section is engageable with a distal end of the annular recess.

11. A syringe, the syringe comprising:
    a barrel body including a body portion that is hollow and configured to be filled with a drug solution, and a cylindrical portion that protrudes in a distal direction from a distal end of the body portion and includes an opening at a distal end of the cylindrical portion, the cylindrical portion defining a flow path that connects an inside of the body portion and the opening;
    a cap including a cap body that is attached to the cylindrical portion, the cylindrical portion includes a female luer section having an inner diameter reduced in a proximal direction from the opening and configured to be engageable with a male luer section of another medical device, and a proximal end section that connects the female luer section to the body portion;
    the cap body includes a base located closer to the distal end than the opening in a state where the cap body is attached to the cylindrical portion, and an insertion portion that protrudes from the base in a proximal direction and configured to be inserted into the cylindrical portion;
    the insertion portion of the cap body includes a first sealing section provided at a distal end of the insertion portion and having an outer diameter greater than a diameter of the opening in a natural state where the cap body is not attached to the cylindrical portion, and a second sealing section provided at a proximal end of the insertion portion and having an outer diameter greater than an inner diameter of the proximal end section of the cylindrical portion in the natural state;
    when the cap body is attached to the cylindrical portion, the first sealing section is configured to seal a distal end section of the flow path in a liquid-tight manner by being compressed radially inward by an inner peripheral surface constituting the opening of the cylindrical portion, and the second sealing section is configured to seal a proximal end section of the flow path in a liquid-tight manner by being compressed radially inward by an inner peripheral surface of the proximal end section of the cylindrical portion;
    the cap further comprising a cylindrical cover member, the cover member having an engagement portion to be engaged with the base of the cap body, and the cover member is configured to be attachable to the cap body so as to cover at least a part of an outer peripheral surface of the base due to an engagement between the engagement portion and the base;
    the cover member includes a cylindrical main body that has the engagement portion and an opening on a distal end of the cylindrical main body, and a distal-end cover member configured to be attached to the opening of the cylindrical main body;

the distal-end cover member including an annular peripheral wall extending in a distal direction from the opening of the cylindrical main body, a distal-end wall provided on a distal end of the annular peripheral wall, and a receiving space defined by the annular peripheral wall and the distal-end wall and configured to receive at least a part of the base;

the annular peripheral wall including a view allowing portion configured to allow an inside of the receiving space to be visible;

the insertion portion of the cap body including a contact portion located closer to a proximal end than the first sealing section and having an outer diameter greater than an inner diameter of the opening of the cylindrical portion;

the cap body configured to be displaceable along an axial direction of the cover member within the cover member from a first position where the base is located within the cylindrical main body to a second position where at least a part of the base protrudes into the receiving space from the opening of the cylindrical main body;

the engagement portion configured to be engageable with the base of the cap body so as to allow movement of the cap body with respect to the cover member in a distal direction, while preventing detachment of the cap body from the cover member in a proximal direction;

the distal-end wall is contactable to a distal end of the cap body so as to prevent detachment of the cap body from the cover member in the distal direction;

the first sealing section configured to seal the distal end section of the flow path in a liquid-tight manner, and the second sealing section configured to seal the proximal end section of the flow path in a liquid-tight manner, in a state where the cap body is located in the first position; and wherein the cap body in the first position is configured to displace to the second position so that an outer periphery of the base is visible through the view allowing portion of the annular peripheral wall, due to a contact between the contact portion of the insertion portion and a distal end section of the cylindrical portion.

12. The syringe according to claim 11, wherein the view allowing portion includes a transparent portion formed in at least a part of the annular peripheral wall.

13. The syringe according to claim 11, wherein the distal-end cover member is made of a transparent material, and the annular peripheral wall entirely serves as the view allowing portion.

14. The syringe according to claim 11, wherein the cover member is made of a material harder than the cap body.

15. A prefilled syringe, the prefilled syringe comprising:
the syringe according to claim 1;
the drug solution filled in the body portion; and
a gasket that is slidable in an axial direction within the body portion in a liquid-tight manner.

16. The prefilled syringe according to claim 15, wherein the drug solution filled in the body portion is a freeze-dried drug solution.

17. The prefilled syringe according to claim 16, further comprising:
an other medical device configured to be filled with another drug solution, the other medical device having a female screw section and a male luer section; and wherein a male screw section on an outer peripheral surface of the cylindrical portion of the syringe is configured to be threaded into the female screw section of the other medical device and the male luer section of the other medical device is configured to be engaged with the female luer section of the cylindrical portion of the syringe.

18. A syringe, the syringe comprising:
a barrel body including a hollow body portion and a cylindrical portion that protrudes in a distal direction from a distal end of the body portion and includes an opening at a distal end of the cylindrical portion, the cylindrical portion defining a flow path that connects an inside of the body portion and the opening;

a cap including a cap body that is attached to the cylindrical portion, the cylindrical portion includes a female luer section having an inner diameter reduced in a proximal direction from the opening and configured to be engageable with a male luer section of another medical device, and a proximal end section that connects the female luer section to the body portion;

the cap body includes a base located closer to the distal end than the opening in a state where the cap body is attached to the cylindrical portion, and an insertion portion that protrudes from the base in a proximal direction and configured to be inserted into the cylindrical portion;

the insertion portion of the cap body includes a first sealing section provided at a distal end of the insertion portion and having an outer diameter greater than a diameter of the opening in a natural state where the cap body is not attached to the cylindrical portion, and a second sealing section provided at a proximal end of the insertion portion and having an outer diameter greater than an inner diameter of the proximal end section of the cylindrical portion in the natural state;

when the cap body is attached to the cylindrical portion, the first sealing section seals a distal end section of the flow path in a liquid-tight manner by being compressed radially inward by an inner peripheral surface constituting the opening of the cylindrical portion, and the second sealing section seals a proximal end section of the flow path in a liquid-tight manner by being compressed radially inward by an inner peripheral surface of the proximal end section of the cylindrical portion;

a cylindrical cover member, the cylindrical cover member including an engagement portion configured to be engaged with the base of the cap body, and wherein the cover member is configured to be attachable to the cap body so as to cover at least a part of an outer peripheral surface of the base due to an engagement between the engagement portion and the base;

the cover member includes a cylindrical main body that has the engagement portion and an opening on a distal end of the cylindrical main body, and a distal-end cover member attached to the opening of the cylindrical main body;

the distal-end cover member including an annular peripheral wall extending in a distal direction from the opening of the cylindrical main body, a distal-end wall provided on a distal end of the annular peripheral wall, and a receiving space defined by the annular peripheral wall and the distal-end wall and capable of receiving at least a part of the base;

the annular peripheral wall including a view allowing portion configured to allow an inside of the receiving space to be visible;

the insertion portion of the cap body including a contact portion located closer to a proximal end than the first sealing section and having an outer diameter greater than an inner diameter of the opening of the cylindrical portion;

the cap body configured to be displaceable along an axial direction of the cover member within the cover member from a first position where the base is located within the cylindrical main body to a second position where at least a part of the base protrudes into the receiving space from the opening of the cylindrical main body;

the engagement portion configured to be engageable with the base of the cap body so as to allow movement of the cap body with respect to the cover member in a distal direction, while preventing detachment of the cap body from the cover member in a proximal direction;

the distal-end wall is contactable to a distal end of the cap body so as to prevent detachment of the cap body from the cover member in the distal direction;

the first seal nq section configured to seal the distal end section of the flow path in a liquid-tight manner, and the second sealing section configured to seal the proximal end section of the flow path in a liquid-tight manner, in a state where the cap body is located in the first position; and wherein the cap body in the first position is configured to displace to the second position so that an outer periphery of the base is visible through the view allowing portion of the annular peripheral wall, due to a contact between the contact portion of the insertion portion and a distal end section of the cylindrical portion.

19. The syringe according to claim 18, wherein the cover member comprises:

a first cover portion, the first cover portion having the engagement portion and configured to cover the outer peripheral surface of the base;

a second cover portion that extends in a proximal direction from the first cover portion and that covers an outer peripheral surface of the cylindrical portion; and wherein the second cover portion has a female screw section on an inner peripheral surface, and the cylindrical portion has a screw portion that is configured to be screwed to the female screw section on the outer peripheral surface.

20. The syringe according to claim 18, wherein the cylindrical main body is made of a substantially opaque material.

* * * * *